United States Patent [19]

Freidlina et al.

[11] 4,029,700
[45] June 14, 1977

[54] PROCESS FOR THE PRODUCTION OF EVEN SERIES ω-AMINO ACIDS

[76] Inventors: Rakhil Khatskelevna Freidlina, ulitsa vavilova, 44, korpus 4, kv. 167; Tamara Trofimovna Vasilieva, ulitsa Vinokurova, 17, korpus 3, kv. 9; Felix Kazimirovich Velichko, ulitsa akademika Vargi, 24, kv. 51; Alexandr Borisovich Terentiev, ulitsa Vinokurova, 17, korpus 3, kv. 9, all of Moscow, U.S.S.R.

[22] Filed: Dec. 24, 1975

[21] Appl. No.: 644,176

[52] U.S. Cl. .................. 260/534 R; 260/482 R; 260/487
[51] Int. Cl.$^2$ ........................... C07C 99/00
[58] Field of Search .................. 260/534 R

[56] References Cited

UNITED STATES PATENTS

| | | | |
|---|---|---|---|
| 2,387,824 | 10/1945 | Block | 260/534 L |
| 2,462,597 | 2/1949 | Block | 260/534 L |
| 2,476,668 | 7/1949 | Kharasch et al. | 260/487 |
| 2,507,568 | 5/1950 | Hanford et al. | 260/487 |
| 3,244,733 | 4/1966 | Wakasa et al. | 260/534 R |
| 3,362,969 | 1/1968 | Tsuchihara | 260/534 R |
| 3,475,489 | 10/1969 | de Graaf et al. | 260/534 R |
| 3,600,434 | 8/1971 | Rust et al. | 260/534 L |

OTHER PUBLICATIONS

Wagner et al., "Synthetic Organic Chemistry," (1953), p. 417.

Primary Examiner—Joseph E. Evans

[57] ABSTRACT

The invention relates to a process for the production of even-series ω-amino acids of the general empirical formula $NH_2(CH_2CH_2)_NCH_2COOH$ /I/, where N = 1 or 2. The process of the invention comprises telomerizing ethylene with methyl esters of halogen acetic acids of the general empirical formula $X_mCH_{3-m}COOCH_3$ /II/, where X = Br and m = 1 or X = Cl and m = 2 or 3, at a temperature of from 100 to 145° C. and under ethylene pressure of from 25 to 40 gage atmospheres in the presence of initiators of free-radical reactions. The telomerization procedure gives telomers of the general empirical formula $CH_3OOCCH_{3-m}X_{m-1}(CH_2CH_2)_nX$ /III/, where X, n and m are as in formulas /I/ and /II/. In case X = Br and m = 1, the telomers described by formula /III/ are subjected to ammonolysis with ammonia at a temperature of about 100° C to yield ammonolysis products; whereas, in case X = Cl and m = 2 or 3, the telomers described by formula /III/ are reduced to telomers of the same general formula, where X = Cl and m = 1, and the latter are subjected to ammonolysis with ammonia at a temperature from 135° to 140° C to yield ammonolysis products. Then the ammonolysis products are hydrolyzed with hydrochloric acid at a temperature of from 80° to 90° C., and the desired product is recovered from the resultant hydrolyzate by use of a styrene-divinylbenzene sulfocationite resin in the H form. The foregoing process uses widely available industrial raw materials, proceeds by a straightforward route and requires simple equipment; it is further characterized by high yields at all steps; all unreacted feedstocks can be completely recycled; and no non-utilizable wastes are produced.

5 Claims, No Drawings

PROCESS FOR THE PRODUCTION OF EVEN SERIES ω-AMINO ACIDS

The present invention relates to processes for manufacturing even-series ω-amino acids which find wide application as medicinals for treating functional disorders of the central nervous system and in surgery. Besides, said acids are employed in industrial chemistry as promotors of polymerization as well as intermediate products in various biochemical syntheses.

No general process for the production of the homologous series of ω-amino acids has so far been developed. It is known in the art to manufacture one of the representatives of said homologous series, viz. γ-aminobutyric acid, by the following methods:

a. Hydrolysis of pyrrolidone to give γ-aminobutyric acid with a yield of 60 to 68 percent.

The disadvantage of said method consists in that pyrrolidone is not available as a ready feedstock and hence has to be manufactured in a process involving several steps. Besides, the resultant product, viz. γ-aminobutyric acid, must be thoroughly purified by repeated washing with alcohol.

b. Biochemical decarboxylation of glutamic acid manufactured from seaweeds.

b. Biochemical decarboxylation of glutamic acid extracted from seaweeds.

The disadvantage of the latter method lies in the limited availability of the feedstock seaweeds.

It is known in the art to produce ε-aminocaproic acid by hydrolysis of caprolactam.

It is known in the art to produce ε-aminocaproic acid by hydrolysis of caprolactam.

The latter process, however, it not a general one and can only be employed for the production of the mentioned acid, among the least valuable in the amino acid series in question.

It is an object of the present invention to provide a process for the production of even-series ω-amino acids of the general empirical formula $NH_2(CH_2CH_2)_n CH_2COOH$ /I/, where $n = 1$ or 2, requiring widely available commerical raw materials and straightforward procedures to be realized.

The foregoing and other objects are attained by that ethylene is telomerized with methyl esters of halogen acetic acids of the general empirical formula $X_mCH_{3-m}COOCH_3$ /II/, where $X = Br$ and $m = 1$ or $X = Cl$ and $m = 2$ or 3, at a temperature of from 100 to 145° C. and under ethylene pressure of from 25° to 40 gage atm. in the presence of initiators of free-radical reactions to produce telomers of the general empirical formula $CH_3OOCCH_{3-m}X_{m-1}(CH_2CH_2)_nX$ /III/, where X, n and m are as described hereabove; in case $X = Br$ and $m = 1$, the telomers described by formula /III/ are subjected to ammonolysis with ammonia at a temperature of about 100° C to yield ammonolysis products; whereas, if $X = Cl$ and $m = 2$ or 3, the telomers described by formula /III/ are reduced to telomers of the same general formula, where $X = Cl$ and $m = 1$, and the latter are subjected to ammonolysis with ammonia at a temperature from 135° to 140° C to give ammonolysis products; the ammonolysis products are further hydrolyzed with hydrochloric acid at a temperature of from 80° to 90° C., and the desired product is recovered from the resultant hydrolyzate by use of a styrene-divinylbenzene sulfocationite resin in the H form.

The process of this invention uses widely available commercial raw materials (ethylene, and methyl esters of halogen acetic acids) and requires simple equipment capable of providing for the requisite mild process conditions (low pressures, moderate temperatures, total lack of aggressive components). It is further characterized by high yields at all steps, and it enables all unreacted feedstock to be recycled. Besides, the proposed process gives no non-utilizable wastes. Finally, the proposed process is characterized by a highly adaptable telomerization step, permitting the process parameters (initiators, temperature and pressure) to be varied with a view to achieving an optimal yield of a specified desired product described by formula /I/ (for $n = 1$, the product is γ-aminobutyric acid used in medicine under the name Gammalon/Daiichi Seiyaku Co. Ltd., Tokyo, Japan/, for $n = 2$, the product is ε-aminocaproic acid).

As has been mentioned above, the telomers of the general formula $CH_3OOCCH_{3-m}X_{m-1}(CH_2CH_2)_nX$ /III/, where $X = Cl$ and $m = 2$ or 3, produced by telomerization, are reduced to telomers of the same general formula, where $X = Cl$ and $m = 1$, the reduction being preferably effected by use of zinc in an aliphatic alcohol at the alcohol boiling temperature. In order to boost the rate of the process, the reduction procedure is preferably carried out in the presence of hydrogen chloride.

The reduction procedure may likewise be effected by means of hydrogen over a palladium catalyst at a temperature of from 20° to 45° C. in the presence of a hydrogen chloride acceptor, viz. tertiary aliphatic amine or ethylene oxide.

All the above-described methods allow of effecting reduction under mild conditions, achieving an almost quantitative yield of the end products.

The process of this invention is preferably realized as follows.

a. Telomerization

The reaction mixture composed of methyl ester of halogen acetic acid of formula /II/, where $X = Br$ and $m = 1$ or $X = Cl$ and $m = 2$ or 3, tertiary butyl peroxide (2.5 percent by weight of the methyl ester) and ethylene (under a pressure of 30 gage atm.), is heated for 3 hours at a temperature of 145° C. with continuous stirring in a stainless steel autoclave. The ethylene pressure is maintained at a constant level throughout the entier process by pumping in fresh ethylene as the reaction gas is being consumed. From the product telomerizate, the starting ester is distilled off to be recycled, and the residue is fractionated under vacuum to yield individual telomers of general formula /III/, where $X = Br$ and $m = 1$ or $X = Cl$ and $m = 2$ or 3.

b. Reduction

The individual telomers of formula /III/, where $X = Cl$ and $m = 2$ or 3 (produced where the feedstock is composed of methyl esters of di- and trichloroacetic acids), are reduced with hydrogen with continuous stirring in the presence of 5 percent by weight of a palladium catalyst (5 percent palladium by weight on a barium sulphate binder) and triethylamine (3 moles per mole of the telomer being reduced), gradually raising the reduction temperature from 20° to 45° C. The end products of the reaction are telomers of general formula /III/, where $X = Cl$ and $m = 1$.

c. Ammonolysis

The individual telomers of general formula /III/, where X = Cl or Br and m = 1, are heated for 6 hours in an air-tight steel vessel containing an alcoholic solution of ammonia (10 moles of ammonia liquor per 1 mole of the starting telomer). In case the telomer of formula /III/ has X = Br, the ammonolysis is preferably carried out at a temperature of 100° C; whereas, if the telomer of formula /III/ has X = Cl, the ammonolysis is preferably effected at a temperature of 140° C. Then the reaction mixture is concentrated by evaporation to produce a dry residue of the ammonolysis products.

d. Hydrolysis

The dry residue of the ammonolysis products is hydrolyzed by boiling with concentrated hydrochloric acid.

e. Recovering the Desired Product from the Hydrolyzate

The resultant hydrolyzate is concentrated by evaporation. The dry residue is dissolved in water, and the liquor thus produced is passed through a column packed with a styrene-divinylbenzene sulfocationite resin in the H form. Having stripped the sulfocationite resin of the chlorine ion with water, the desired product amino acid is eluted with a 5-percent aqueous solution of ammonia. Then the eluate is concentrated by evaporation to give the desired product (γ-aminobutyric or ε-aminocaproic acid) in the form of dry residue.

The invention will be further understood from the following examples illustrating the proposed process for the production of even ω-aminoacids of general formula /I/.

EXAMPLE 1

Manufacture of γ-Aminobutyric and ε-Aminocaproic Acids from Methyl Bromacetate a. Methyl Esters of γ-Bromobutyric and ε-Bromocaproic Acids 136 g of methylbromacetate and 3.5 g of azo-bis-isobutyronitrile are charged at 20° C. into a rotary stainless steel autoclave of capacity 0.27 lit provided with a heating jacket and a thermocouple, after which ethylene is added with stirring until the pressure in the autoclave reaches 40 gage atm. Then, within 20 minutes, the temperature in the autoclave is brought to 100° C., and the stirring is carried on at the latter temperature until the pressure ceases to drop, which takes approximately 2 to 3 hours. The remaining ethylene is allowed to escape. The telomerizate (129 g) is subjected to fractional distillation under vacuum, the unreacted methylbromacetate (101 g) being distilled off at a temperature of 80 to 83° C. and a residual pressure of 80 mm Hg. The remaining telomer mixture (27 g) is subjected to fractional distillation in a fractionating column at a residual pressure of 10 mm Hg to yield 14g of methyl ester of γ-bromobutyric acid (35 percent in terms of the reacted methylbromacetate) having a boiling point of 75° to 78° C./10 mm Hg or 124° C./100 mm Hg. The distillation residue (9 g, or 18 percent in terms of the reacted methylbromacetate) is methyl ester of ε-bromocaproic acid having a boiling point of 116° C./12 mm Hg.

b. γ-Aminobutyric Acid 55 ml of methanol saturated with ammonia (14.6 g $NH_3$) at 0° C. and 18.1 g of methyl ester of γ-bromobutyric acid are charged into a 0.5-liter stainless steel autoclave. The autoclave contents are heated to a temperature of about 100° C and maintained at said temperature for 6 hours. The resultant mixture is concentrated by evaporation under vacuum; the residue is mixed with 50 ml of concentrated hydrochloric acid; the mixture is heated to a temperature of from 82 to 83° C., maintained at said temperature for 6 hours and evaporated under vacuum to give 23.4 g of dry residue which is dissolved in water to produce a 10-percent solution (224 ml). The solution is passed through a column packed with a styrene-divinylbenzene sulfocationite resin in the H form. Then the sulfo cationite resin is stripped of the chlorine ion with water, and the desired amino acid is eluted with a 5-percent aqueous solution of ammonia. The ammonia liquor is concentrated by evaporation to yield 6.2 g of γ-aminobutyric acid which, after being washed with hot ethanol, has a melting point of 192° C. and is chromatographically indistinguishable from the commercial drug Gammalon. The yield of γ-aminobutyric acid is 50 percent of the theoretical in terms of methyl ester of γ-bromobutyric acid.

c. ε-Aminocaproic Acid

The ammonolysis and hydrolysis procedures duplicate those employed for producing γ-aminobutyric acid.

A mixture of 12.6 g of the methyl ester of ε-bromocaproic acid produced at the telomerization step and 40 ml of methanol saturated with ammonia (10.2 g of ammonia) at 0° C. is charged into a 0.5-liter stainless steel autoclave. Having been kept at a temperature of 100° C. for 6 hours, the mixture is concentrated by evaporation under vaccum, the residue is washed with 10 ml of absolute ether and heated with 30 ml of concentrated hydrochloric acid for 10 hours at a temperature between 85° and 90° C. The solution is evaporated under vacuum, and 126 ml of water is added to the evaporation residue (14.3 g). The aqueous solution thus prepared is neutralized with several drops of ammonia and passed through a column packed with a styrene-divinyl benzene sulfo cation exchanger in the H form. After the sulfocationite resin has been stripped of the chlorine ion with water, the desired amino acid is eluted with a 5-percent aqueous solution of ammonia. The resultant 250 ml of the eluate is concentrated by evaporation under vacuum. The residue (6.5 g) is washed 4 times with 5 ml of cold absolute ethanol, to give the end product, viz. pure ε-aminocaproic acid of melting point 203° to 204° C., which agrees with the data published by the other authors. The yield of ε-aminocaproic acid is 60 percent of the theoretical in terms of methyl ester of ε-bromocaproic acid.

EXAMPLE 2

Manufacture of γ-Aminobutyric acid ε-Aminocaproic Acids from Methyltrichloroacetate a. Methyl Esters of α, α, γ-Trichlorobutyric and α, α, ε-Trichlorocaproic Acids A 0.5-liter enamel autoclave is charged with 178 g of methyltrichloroacetate and 3 ml of tertiary butyl peroxide, after which ethylene is supplied into the autoclave until the pressure therein reaches 25 gage atm., whereupon telomerization is initiated at a temperature of from 140° to 145° C. The telomerization procedure is carried on for 2 to 3 hours. The combined telomerizate from 6 runs is subjected to fractional distillation in a fractionating column, distilling off 820 g of unreacted methyltrichloroacetate. The remaining 240 g of the telomer mixture is subjected to fractional distillation to give 215 g (75 percent in terms of the reacted methyltrichloroacetate) of methyl ester of $\alpha$, $\alpha$, $\gamma$-trichlorobutyric acid of boiling point between 107.5 and 108.5° C./25 mm Hg and $n_D^{20}$ = 1.4731. The residue is constituted by 20 g of methyl ester of $\alpha$, $\alpha$, $\epsilon$-trichlorocaproic acid having a boiling point of 81° C./1 mm Hg, $n_D^{20}$ = 1.4755 and $d_4^{20}$ = 1.3120 b. Ethyl Ester of $\gamma$-Chlorobutyric Acid

Methyl ester of $\alpha$, $\alpha$, $\gamma$-trichlorobutyric acid is reduced with zinc dust in ethanol. To this end, a solution of 2g of methyl ester of $\alpha$, $\alpha$, $\gamma$-trichlorobutyric acid in 13ml of ethanol is added to 2 g of zinc dust, and the resultant liquor is boiled for 4 hours. Upon completion of the reaction, the liquor, which is shown by gas-liquid chromatography to contain ethyl ester of $\gamma$-chlorobutyric acid, is decanted and diluted with water, after which the ethyl ester of $\gamma$-chlorobutyric acid is extracted with chloroform or ether. The extract is dried over calcium chloride, the solvent is distilled off, and the residue is distilled under vacuum to give 1.2 g (80 percent of the theoretical) of ethyl ester of $\gamma$-chlorobutyric acid of boiling point 80° to 81° C./20 mm Hg and $n_D^{20}$ = 1.4315.

c. Methyl Ester of $\epsilon$-Chlorocaproic Acid

Methyl ester of $\alpha$, $\alpha$, $\epsilon$-trichlorocaproic acid is reduced in a procedure similar to that described under (b) of Example 2. The product is methyl ester of $\epsilon$-chlorocapronic acid of boiling point 100° C./16 mm Hg, $n_D^{20}$ = 1.4430 and $d_4^{20}$ = 1.0710. The yield of the ester amounts to 90 percent of the theoretical.

d. $\gamma$-Aminobutyric and $\epsilon$-Amincaproic Acids

The above-described alkyl esters of $\omega$-chloroacids are ammonolyzed in a procedure duplicating those described in Example 1 (under (b) and (c)) at a temperature of from 135° to 140° C. The hydrolysis of the ammonolysis products and the recovering of the desired products from the hydrolyzate are carried out in procedure likewise duplicating those of Example 1 (under (b) and (c)).

EXAMPLE 3

Manufacture of $\gamma$-Aminobutyric and $\epsilon$-Aminocaproic Acids from Methyl Trichloroacetate The telomerization, reduction, ammonolysis, hydrolysis and recovery of the desired products are all carried out in procedures duplicating those of Example 2, the only difference being that the reduction is accompanied by the passage through the reaction mixture of gaseous hydrogen chloride, thereby cutting down the reaction time to 1 hour.

EXAMPLE 4

Manufacture of $\gamma$-Aminobutyric and $\epsilon$-Aminocaproic Acids from Methyl Trichloroacetate The telomerization, ammonolysis, hydrolysis and recovery of the desired products are carried out in procedures duplicating those of Example 2, except that the reduction of methyl ester of $\alpha$, $\alpha$, $\gamma$-trichlorobutyric acid is effected with hydrogen over a palladium catalyst. To this end, a hydrogenation vessel is charged with 2 g of a palladium catalyst (5 percent palladium by weight on barium sulfate), 1 ml of glacial acetic acid and 20 ml of methanol, after which the catalyst is activated with hydrogen for 15 to 20 minutes. Then the vessel is charged with a mixture of 29 g of methyl ester of $\alpha$, $\alpha$, $\gamma$-trichlorobutyric acid, 40 g of triethylamine (3 moles triethylamine per 1 mole ester) and 70 ml of methanol, whereupon said ester is hydrogenated with hydrogen, raising the temperature from 20° to 45° C. until a theoretical quantity of hydrogen (6.6 lit) has been consumed. The reaction mixture is neutralized with 19 ml of 15-percent hydrochloric acid, and the catalyst in filtered off. The methanol is distilled off from the filtrate at a pressure of between 600 and 700 mm Hg until a crystalline mass is formed in the still (the distillate contains about 60 ml of methanol). The crystalline mass is dissolved in 50 ml of water, and the resultant liquor is extracted with ether or chloroform. After washing the extract with water and drying it over calcium chloride, the solvent is distilled off and the residue is distilled under vacuum to yield 13.7 g (70 percent of the theoretical) of methyl ester of $\gamma$-chlorobutyric acid of boiling point 87° to 89° C./33 mm Hg and $n_D^{20}$ = 1.4330.

Methyl ester of $\alpha$, $\alpha$, $\epsilon$-trichlorocaproic acid is reduced in a procedure duplicating that used to reduce methyl ester of $\alpha$, $\alpha$, $\gamma$-trichlorobutyric acid, obtaining methyl ester of $\epsilon$-chlorocaproic acid of boiling point 100° C./16 mm Hg, $n_D^{20}$ = 1.4430 and $d_4^{20}$ = 1.0710. The ester yield amounts to 90 percent of the theoretical.

EXAMPLE 5

Manufacture of $\gamma$-Aminobutyric and $\epsilon$-Aminocaproic Acids from Methyl Trichloroacetate The telomerization, ammonolysis, hydrolysis and desired product recovery steps are effected in procedures duplicating those of Example 2. The reduction procedure duplicates that of Example 4, except that the triethylamine is replaced by ethylene oxide in the same molar ratio to the ester being reduced.

EXAMPLE 6

Manufacture of $\gamma$-Aminobutyric Acid from Methyldichloroacetate a. Methyl Ester of $\alpha$, $\gamma$-Dichlorobutyric Acid In this example, ethylene is telomerized with methyldichloroacetate in a procedure duplicating that of Example 2 (under (a)), except that the initiator of telomerization is a solution of iron or cobalt carbonyls in isopropyl alcohol (in the molar ratio of 1 alcohol to 1 methyldichloroacetate and 1 carbonyl to 20 alcohol) rather than the tertiary butyl peroxide. As soon as the telomerization process is over, the reaction mixture is passed through a column packed with silica gel (to remove the metal salts), the alcohol is distilled off, and the residue, viz. a mixture of the telomers, is subjected to fractionation, as described in Example 2, to recover methyl ester of $\alpha$, $\gamma$-dichlorobutyric acid with a yield of 50 percent of the theoretical.

b. Methyl Ester of γ-Chlorobutyric Acid

Methyl ester of α, γ-dichlorobutyric acid is reduced with hydrogen over a palladium catalyst. To this end, 17.1 g of methyl ester of α, γ-dichlorobutyric acid is hydrogenated with hydrogen at a temperature of from 40° to 45° C. in 50 ml of methanol over 2 g of 5-percent palladium on barium sulphate in the presence of 14 g of ethylene oxide. The process is carried on until a theoretical quantity (2.3 lit) of hydrogen has been consumed. Then the catalyst is filtered off, the methanol and ethylenechlorohydrin are distilled off from the filtrate at atmospheric pressure, and the residue is distilled under vacuum to yield 11 g (80 percent of the theoretical) of methyl ester of γ-chlorobutyric acid of boiling point 88° C./ 33 mm Hg and $n_D^{20} = 1.4328$.

c. γ-Aminobutyric Acid

The ammonolysis of methyl ester of γ-chlorobutyric acid as well as the subsequent stages of hydrolysis and desired product recovery from the hydrolyzate are effected using procedures duplicating those of Example 2 (under (d)).

What is claimed is:

1. A process for the production of even series ω-amino acids of the general empirical formula $NH_2(CH_2CH_2)_nCH_2COOH$ (I), where n is the integer 1 or 2, wherein ethylene is telomerized with methyl esters of halogen acetic acids of the general empirical formula $X_mCH_{3-m}COOCH_3$ (II), where X and M are as follows:
   X = Cl, m is the integer 2 or 3; said telomerization is effected at a temperature in the range from 100 to 145° C. and under ethylene pressure in the range from 25 to 40 gage atmospheres in the presence of initiators of free-radical reactions; said telomerization producing telomers of the general empirical formula $CH_3OOCCH_{3-m}X_{m-1}(CH_2CH_2)_nX$ (III), where X, n and m are the same as in the formulas hereabove; which are reduced to telomers of the same general formula, where X = Cl and m = 1, and the latter are subjected to ammonolysis with ammonia at a temperature from 135° to 140° C to yield ammonolysis products; the ammonolysis products are further hydrolyzed with hydrochloric acid at a temperature in the range from 80° to 90° C.; the desired product is recovered from the resultant hydrolyzate by use of a styrene-divinylbenzene sulfocationite resin in the H form.

2. A process as set forth in claim 1, wherein the reduction is effected by use of zinc in an aliphatic alcohol at the alcohol boiling temperature.

3. A process as set forth in claim 2, wherein the reduction is carried out in the presence of hydrogen chloride.

4. A process as set forth in claim 1, wherein the reduction is effected by use of hydrogen over a palladium catalyst at a temperature in the range from 20° to 45° C. in the presence of a hydrogen chloride acceptor selected from the group consisting of tertiary aliphatic amine and ethylene oxide.

5. A process for the production of even series ω-amino acids of the general empiricol formula $NH_2(CH_2CH_2)_nCH_2COOH$ (I), where n is the integer 1 or 2, wherein ethylene is telomerized with methyl esters of halogen acetic acids of the general empirical formula $X_mCH_{3-m}COOCH_3$ (II), where X and m are as follows:
   X = Br, m = 1; said telomerization is effected at a temperature in the range from 100° to 145° C. and under ethylene pressure in the range from 25 to 40 gage atmospheres in the presence of initiators of free-radical reactions; said telomerization producing telomers of the general empirical formula $CH_3OOCCH_{3-m}X_{m-1}(CH_2CH_2)_nX$ (III), where X, n and m are the same as in the formulas hereabove; which are subjected to ammonolysis with ammonia at a temperature of about 100° C to yield ammonolysis products; the ammonolysis products are further hydrolyzed with hydrochloric acid at a temperature in the range from 80° to 90° C.; the desired product is recovered from the resultant hydrolyzate by use of a styrene-divinylbenzene sulfocationite resin in the H form.

* * * * *